(12) United States Patent (10) Patent No.: US 8,927,730 B2
Silverman et al. (45) Date of Patent: Jan. 6, 2015

(54) INTRAMOLECULAR HYDROGEN-BONDED NITRIC OXIDE SYNTHASE INHIBITORS

(75) Inventors: Richard B. Silverman, Northbrook, IL (US); Fengtlan Xue, Baton Rouge, LA (US)

(73) Assignee: Northwestern University, Evanston, IL (US)

( * ) Notice: Subject to any disclaimer, the term of this patent is extended or adjusted under 35 U.S.C. 154(b) by 92 days.

(21) Appl. No.: 13/250,554

(22) Filed: Sep. 30, 2011

(65) Prior Publication Data

US 2012/0088798 A1 Apr. 12, 2012

Related U.S. Application Data

(60) Provisional application No. 61/388,375, filed on Sep. 30, 2010.

(51) Int. Cl.
| | | |
|---|---|---|
| *C07D 401/00* | (2006.01) | |
| *A01N 43/40* | (2006.01) | |
| *A61K 31/44* | (2006.01) | |
| *C07D 405/14* | (2006.01) | |
| *C07D 401/06* | (2006.01) | |
| *C12N 9/99* | (2006.01) | |

(52) U.S. Cl.
CPC ............ *C07D 401/06* (2013.01); *C07D 405/14* (2013.01); *C12N 9/99* (2013.01)
USPC ....................... 546/278.4; 514/343

(58) Field of Classification Search
USPC .......................................... 546/278; 514/343
See application file for complete search history.

(56) References Cited

U.S. PATENT DOCUMENTS 7,470,790 B2 12/2008 Silverman et al.
7,994,326 B2 8/2011 Silverman et al.

FOREIGN PATENT DOCUMENTS

WO WO 2008042353 A1 * 4/2008

OTHER PUBLICATIONS

Sheridan, R.P. "Common Chemical Replacements in Drug-Like Compounds"J. Chem. Inf. Comput. Sci, 2002, vol. 42, pp. 103-108.*
U.S. Appl. No. 13/174,982, filed Jul. 1, 2011, Silverman et al.
U.S. Appl. No. 61/360,727, filed Jul. 1, 2010, Silverman et al.
Delker, Ji, Li, Jamal, Fang, Xue, Silverman and Poulos, "Unexpected Binding Modes of Nitric Oxide Synthase Inhibitors Effective in the Prevention of a Cerebral Palsy Phenotype in an Animal Model", J. Am. Chem. Soc., 2010, 132, 5437-5442.
Fang and Silverman "A Cellular Model for Sreening Neuronal Nitric Oxide Synthase Inhibitors", Analytical Biochemistry 390 (2009) 74-78.
Hevel and Marietta, "Nitric-Oxide Synthase Assays", Methods in Enzymology, 1994, vol. 233, 250-258.
Hevel, White and Marietta, "Purification of the Inducible Murine Macrophage Nitric Oxide Synthase", J. Biol. Chem. 1991, vol. 266, No. 34, 22789-22791.
Ji, Tan, Igarashi, Li, Derrick, Mrasek, Roman, Vasquez-Vivar, Poulos and Silverman, "Selective Neuronal Nitric Oxide Synthase Inhibitors and the Prevention of Cerebral Palsy", American Neurological Association, 2009, 65, 209-217.
Lawton, Ranaivo, Chico, Ji, Xue, Partasek, Roman, Watterson and Silverman, "Analogues of 2-aminopyridine-based selective inhibitors of neuronal nitric oxide synthase with increased bioavailability", Bioorganic & Medicinal Chemstry 17 (2009) 2371-2380.
Silverman, "Design of Selective Neuronal Nitric Oxide Synthase Inhibitors for the Prevention and Treatment of Neurodegenerative Diseases", Accounts of Chemical Research, vol. 42, Mar. 2009, 439-451.
Xue, Fang, Lewis, Martasek, Roman and Silverman, "Potent and Selective Neuronal Nitric Oxide Synthase Inhibitors with Improved Cellular Permeability", Bioorganic & Medicinal Chemistry Letters 20 (2010) 554-557.
Xue, Huang, Ji, Fang, Li, Martasek, Roman, Poulos and Silverman, "Structure-Based Design, Synthesis, and Biological Evaluation of Lipophilic-Tailed Monocationic Inhibitors of Neuronal Nitric Oxide Synthase", Bioorganic & Medicinal Chemistry 18 (2010) 6526-6537.

* cited by examiner

*Primary Examiner* — Kendra D Carter
(74) *Attorney, Agent, or Firm* — Reinhart Boerner Van Deuren s.c

(57) ABSTRACT

Compounds and related compositions and methods as can be used to selectively inhibit neuronal nitric oxide synthase and as can be employed in the treatment of various neurodegenerative diseases.

10 Claims, 3 Drawing Sheets
(2 of 3 Drawing Sheet(s) Filed in Color)

INTRAMOLECULAR HYDROGEN-BONDED NITRIC OXIDE SYNTHASE INHIBITORS

This application claims priority benefit from application Ser. No. 61/388,375 filed Sep. 30, 2010, the entirety of which is incorporated herein by reference.

This invention was made with government support under Grant No. R01 GM049725 awarded by the National Institutes of Health. The government has certain rights in the invention.

BACKGROUND OF THE INVENTION

Neurodegenerative disorder has become a rapidly spreading health crisis in the United States. It affects millions of Americans today, and costs hundreds of billions of dollars to provide caring for the patients annually. Despite the tremendous effort in research aim to discover new medicines, most neurodegenerative diseases remain incurable. According to this situation, there is an urgent need for the development of novel neurodegenerative therapeutic agents. Historically, the abnormally high concentration of cerebral nitric oxide (NO), the product of the neuronal isoform of nitric oxide syntheses (nNOS), has been observed as a key pathogenic phenomenon shared by various neurodegenerative conditions including chronic pathologies such as Alzheimer's, Parkinson's, Huntington's, headaches, as well as neuronal damage in stroke. Such observations provide a rationale for the therapeutic use of nNOS inhibitors as a general treatment for neurodegeneration. In the past two decades, a large number of nNOS inhibitors have been reported, but most have met with limited success.

Recently, cis-3,4-pyrrolidine inhibitors (e.g., 1 and 2, FIG. 1) were developed using structure-based drug design. (See, e.g., Silverman, R. B. Design of selective neuronal nitric oxide synthase inhibitors for the prevention and treatment of neurodegenerative diseases. Acc. Chem. Res. 2009, 42, 439 451; Delker, D. L.; Ji, H.; Li, H.; Jamal, J.; Fang, J.; Xue, F.; Silverman, R. B.; Poulos, T. L. Unexpected binding modes of nitric oxide synthase inhibitors effective in the prevention of cerebral palsy. J. Am. Chem. Soc. 2010, 132, 5437 5442; Ji, H.; Tan, S.; Igarashi, J.; Li, H.; Derrick, M.; Martásek, P.; Roman, L. J.; Vásquez Vivar, J.; Poulos, T. L.; Silverman, R. B. Selective neuronal nitric oxide synthase inhibitors for prevention of cerebral palsy. Ann. Neural. 2009, 65, 209 217; and Lawton, G. R.; Ranaivo, H. R.; Wing, L. K.; Ji, H.; Xue, F.; Martesek, P.; Roman, L. J.; Watterson, D. M.; Silverman, R. B. Analogues of 2-aminopyridine-based selective inhibitors of neuronal nitric oxide synthase with increased bioavailability. Bioorg. Med. Chem. 2009, 17, 2371 2380.) These inhibitors showed excellent potency and isoform selectivity for nNOS over endothelial NOS and inducible NOS, which made them promising candidates for treatment of neurodegenerative diseases. To target nNOS and exhibit pharmaceutical activity in the brain, such candidates also need to penetrate the blood brain barrier (BBB), a unique barrier formed by brain capillary endothelial cells. However, animal test results indicated that the pyrrolidine inhibitors (e.g., 1 and 2) do not penetrate the BBB. Presumably, from a structural perspective, the amino groups of 1 and 2 are positively charged at physiological pH, inhibiting BBB penetration.

To circumvent this challenge, different strategies have been developed to tune the chemical structures of 1 and 2 and increase lipophilicity without impairing potency and selectivity. For example, the high $pK_a$ amino groups were replaced by neutral functionalities such as ethers and amides. (See, Lawton, G. R.; Ranaivo, H. R.; Wing, L. K.; Ji, H.; Xue, F.; Martesek, P.; Roman, L. J.; Watterson, D. M.; Silverman, R. B. Analogues of 2-aminopyridine-based selective inhibitors of neuronal nitric oxide synthase with increased bioavailability. Bioorg. Med. Chem. 2009, 17, 2371-2380.) Different electron-withdrawing groups, such as ether, difluoromethylene, and cyclopropyl groups, were incorporated next to the amino group in the lipophilic tail to partially remove the positive charge of the amino group at physiological pH. (See, Xue, F.; Fang, J.; Lewis, W. W.; Martasek, P.; Roman, L. J.; Silverman, R. B. Potent and selective neuronal nitric oxide synthase inhibitors with improved cellular permeability. Bioorg. Med. Chem. Lett. 2010, 20, 554 557; and Xue, F.; Huang, J.; Ji, H.; Fang, J.; Li, H.; Martásek, P.; Roman, L. J.; Poulos, T. P.; Silverman, R. B. Structure-based design, synthesis, and biological evaluation of lipophilic-tailed monocationic inhibitors of neuronal nitric oxide synthase. Bioorg. Med. Chem. 2010, 18, 6526-6537). While such modifications provided a new generation of pyrrolidine inhibitors with improved membrane and BBB permeability, the potency and isoform selectivity of some such components were somewhat compromised.

SUMMARY OF THE INVENTION

In light of the foregoing, it is an object of the present invention to provide compounds, compositions and related methods of use for the selective inhibition of neuronal nitric oxide synthase, thereby overcoming various deficiencies and shortcomings of the prior art including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule compounds exhibiting selective nNOS inhibition over other enzyme isoforms and providing improved membrane permeability and bioavailability.

It can be another object of the present invention to provide an enantiomerically pure compound to effect binding orientation and improved potency and selective activity over corresponding racemic mixtures.

It can be an object of the present invention to provide one or more NOS inhibitor compounds alternately exhibiting sufficient lipophilicity to penetrate cellular membranes and/or the brain blood barrier, and maintaining potency and selectivity for the neuronal isoform.

It can be another object of the present invention to provide such selective NOS inhibitor compounds capable of intramolecular hydrogen bonding and change in molecular conformation sufficient for both such membrane/barrier penetration and inhibition, depending upon chemical and physical environment.

It can be another object of the present invention to provide one or more such compounds for in vitro use and study under conditions promoting nitric oxide production, indicative of one more mammalian disease states.

Alternatively, it can be an object of the present invention to provide one or more such compounds enabling in vivo treatment of any such disease state.

Other objects, features, benefits and advantages of the present invention will be apparent from this summary and the following descriptions of certain embodiments of such compounds, compositions and/or methods, and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

In part, the present invention can be directed to compounds of a formula

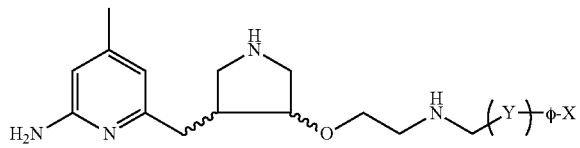

together with salts, hydrates and/or solvates of such compounds, and to pharmaceutical compositions comprising one or more such compounds, optionally together with an acceptable carrier component, such a compound wherein Y can be a covalent bond or selected from C(O) and CH$_2$C(O) moieties; Φ can be a moiety selected from aryl and heteroaryl moieties; and X can be selected from electron-withdrawing groups and unshared electron pairs, such groups and electron pairs as can be positioned on such a Φ moiety sufficient for intramolecular hydrogen-bonding with the pendent secondary amino group of such a compound. More generally, such moieties/groups and/or substituents thereof are limited only by electron-withdrawing function, as can be considered in the context of mitigation or partial removal of a degree of positive charge from an amine functionality, such as at physiological pH. Accordingly, without limitation, in certain such embodiments, such a compound can be present as an acid salt, either partially or fully protonated. In certain such embodiments, the counter ion(s) can be a conjugate base of a protic acid.

In certain non-limiting embodiments, Φ can be selected from phenyl and furanyl moieties, and can be optionally substituted by one or more groups R to further affect and/or enhance intramolecular H-bonding or otherwise affect nitric oxide synthase inhibition. Regardless, in certain such embodiments, Φ can be phenyl, and X can be selected from fluoro, hydroxy and methoxy groups. Alternatively, in certain other embodiments, Φ can be a furanyl moiety, and X can be an unshared electron pair. With respect to broader aspects of this invention, the present compounds are without stereochemical limitation. Where such compounds and/or their intermediates are available as racemic mixtures, the respective isomers can be resolved. Likewise, as such compounds are diastereomers, the corresponding enantiomers can be separated. Accordingly, any such stereocenter can be (S) or (R) with respect to any other stereocenter(s), whether such a compound is present as a salt, hydrate and/or solvate thereof. Without limitation, such a compound can be selected from the (S,S) and (R,R) enantiomers.

As such, the present invention can, in part, be directed to certain compounds of a formula wherein X can be selected from the fluoro, hydroxy and methoxy groups, and salts of such compounds. In certain embodiments, X can be either fluoro or methoxy. Notwithstanding identity of X, one or more groups R can be present to affect and/or enhance intramolecular H-bonding or otherwise affect nitric oxide synthase inhibition. Regardless, such a compound can be complexed with, bound to or otherwise in contact or associated with a nitric oxide synthase.

In part, the present invention can be directed to a composition comprising a compound of the sort described above in a medium affecting compound conformation. In certain embodiments, such a medium can be a lipophilic cellular medium absent a nitric oxide synthase. In certain such embodiments, such a compound can be in a conformation where hydrogen-bonding is present between hydrogen-acceptor/donor X and the secondary amino group of such a compound. In certain other embodiments, such a medium can comprise a nitric oxide synthase. In certain such embodiments, such a compound can be in a conformation substantially absent intramolecular hydrogen-bonding with the secondary amino group of such a compound.

In part, the present invention can be directed to a method of using molecular conformation to affect bioavailability of a nitric oxide synthase inhibitor compound. Such a method can comprise providing a compound of the sort described herein; and contacting such a compound with a medium affecting intramolecular hydrogen-bonding between acceptor/donor X and the secondary amino group of such a compound. Bioavailability can be assessed by one or more cell-based assays of the sort understood by those skilled in the art, including without limitation the cell-based assay described elsewhere herein, and corresponding inhibition of nitric oxide production indicating membrane permeability and effective compound cellular concentration.

In certain non-limiting embodiments, such a medium can comprise a nitric oxide synthase. In certain such embodiments, such a medium, whether in vivo or in vitro, can induce conformation of such a compound substantially absent intramolecular hydrogen bonding. In certain other embodiments, such a medium can be lipophilic and absent a nitric oxide synthase. In certain such embodiments, such a medium can induce conformation of such a compound with hydrogen-bonding between acceptor/donor X and the secondary amino group thereof. Such a medium can be in vivo or, alternatively, can model either a cellular membrane or a brain blood barrier. Regardless, such a medium can comprise a physiological pH.

In part, the present invention can also provide a method of inhibiting a nitric oxide synthase. Such a method can comprise contacting a nitric oxide synthase with an effective amount of any one or more of the present compounds, including but not limited to those illustrated by the following examples, referenced figures and/or accompanying synthetic schemes. As discussed above, in certain embodiments, Φ can be selected from phenyl and furanyl, and such a compound can be selected from the (S,S) and (R,R) enantiomers. With regard to the latter, where such a compound is present as the (R,R) enantiomer, such a method can be selective for inhibition of neuronal nitric oxide synthase.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF CERTAIN EMBODIMENTS

Figure 1:
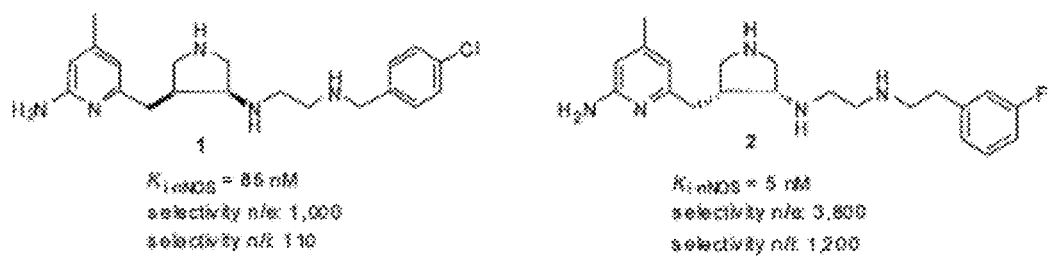
FIG. 1. Chemical structure and inhibitory activity of prior art compounds 1 and 2.
Figure 2:
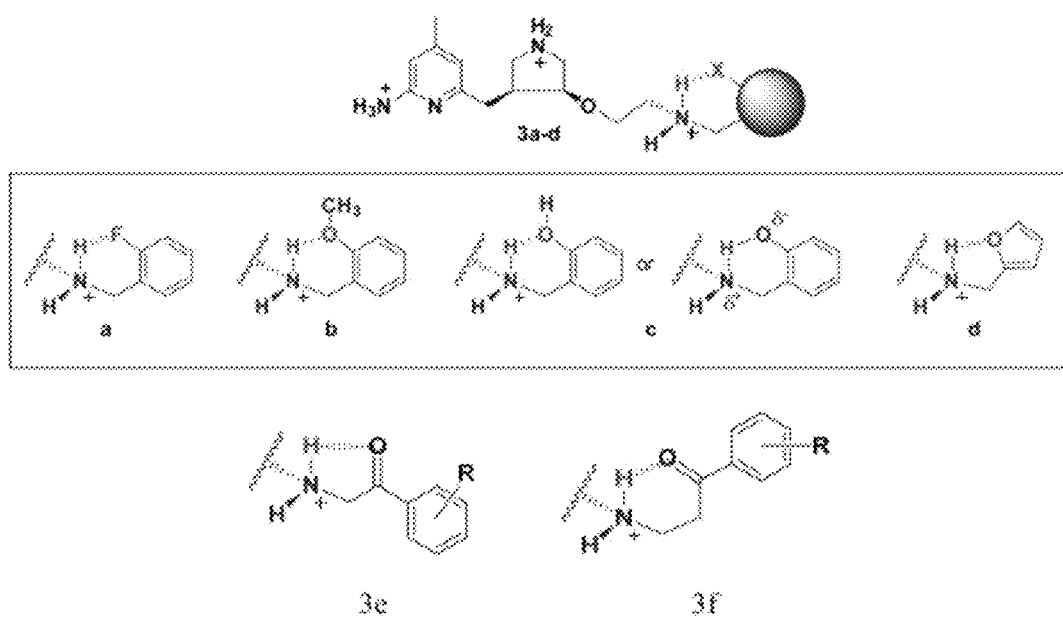
FIG. 2. Chemical structures of inhibitor compounds 3a-f, in accordance with several non-limiting embodiments of this invention.

The design and synthesis of certain nNOS inhibitors (e.g., without limitation, compounds 3a-f, FIG. 2) of this invention can be considered 1) through replacement of the amino group on the chiral pyrrolidine ring of compound 1 by an oxygen atom, and 2) with a hydrogen bond acceptor/donor group (X) incorporated into the aromatic tail. It was hypothesized that an intramolecular hydrogen bond can influence inhibitor membrane and BBB permeability while not compromising inhibitory activity. Without limitation to any one theory or mode of operation in cell-membrane or the BBB, where the chemical environments are highly hydrophobic, the inhibitors can be considered to form an intramolecular hydrogen bond and adopt a "closed" conformation, which show lower overall polarity and improved BBB permeability by the mechanism of passive diffusion. Conversely, the inhibitors bind to nNOS with an "open" conformation, similar to parent compound 1, in which the secondary amino group is released from the intramolecular hydrogen bonding. A simple, colorimetric, cell-based assay using HEK293t cells stably transfected with rat nNOS was employed to assess the membrane permeability of such compounds, and crystal structures show that the "open" conformation is indeed achieved when these inhibitors are in the nNOS active site.

The synthesis of inhibitors 3a-d used chiral precursor 4. (See, co-pending application Ser. No. 61/360,727 filed Jul. 1, 2010, the entirety of which is incorporated herein by reference, for preparation of the pyrrolidine 3,4-cis and -trans diastereomers; Scheme 1, below.) Allylation of (3S,4S) pyrrolidine intermediate 4 using allyl methyl carbonate in the presence of Pd(PPh₃)₄ gave alkene 5 in good yield. Alkene ozonolysis provided aldehyde 6, which was then subjected to reductive amination with various methanamines to yield the corresponding secondary amines 7a-d. Finally, the three Boc-protecting groups were removed concurrently in TFA to generate inhibitors 3a-d. Likewise, as would be understood by those skilled in the art and made aware of this invention, aldehyde 6 can be reacted with suitably protected 2-oxoethanamine or 3-oxopropanamine en route to inhibitor compounds 3e and 3f, respectively. (See, e.g., FIG. 2 where, without limitation, R can represent one or more halo substituents (e.g., F, Cl, etc.) of the sort to affect NOS inhibition.)

Scheme 1. Synthesis of 3a-d.

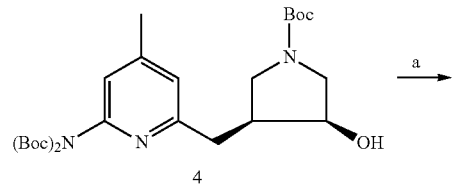

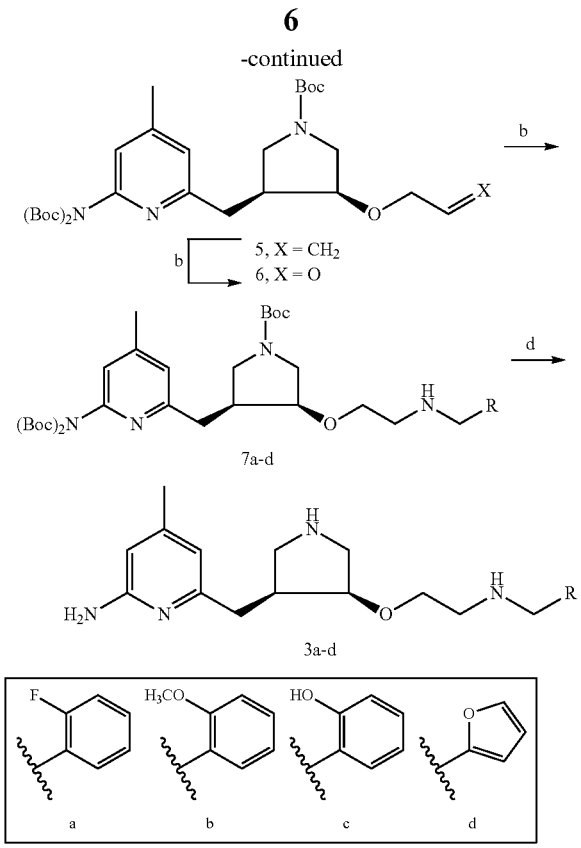

*Reagents and conditions: (a) allyl methyl carbonate, Pd(PPh₃)₄, 45° C., 5 h, 66%; (b) O₃, -78° C., 30 min, (ii) Me₂S, -78° C. to rt, 2 h, 87%; (c) amines, NaHB(OAc)₃, rt, 3 h, 91%; (d) 6N HCl in MeOH (2:1), rt, 12 h, 99%.

While the present invention can be illustrated in the context of a 4-methylpyridine moiety conjugated with a pyrrolidine core, will be understood by those skilled in the art that heterocycle conjugation via alkylation and pyrrolidine epoxide ring-opening can be achieved with various other haloalkylpyridine and other haloalkylheterocyclic moieties. For example, without limitation, various other heterocyclic moieties including but not limited to substituted and unsubstituted thiazine, oxazine, pyrazine, oxazole and imidazole moieties are described in U.S. Pat. No. 7,470,790 issued Dec. 30, 2008 and co-pending application Ser. No. 11/906,283 filed Oct. 1, 2007, in the context of substructures I and III as discussed more fully therein, each of which is incorporated herein by reference in its entirety. The corresponding chiral pyrrolidine core compounds can be prepared using synthetic techniques of the sort described herein or straight forward modifications thereof, as would be understood by those skilled in the art and made aware of this invention. Such heterocycle-conjugated compounds, analogous to core compound 4, above, can be used en route to NOS inhibitors, including selective nNOS inhibitors, of the sort described in the aforementioned incorporated references.

The potencies of these compounds were tested in vitro both in a purified enzyme assay and in a cell-based assay using 293t cells stably transfected with rat nNOS. The purified enzyme assay results demonstrate that compounds 3a-d maintain adequate potency for nNOS in comparison with previous inhibitors 1 and 2 (Table 1). Furthermore, these compounds retain some selectivity over the iNOS and eNOS isoforms.

TABLE 1

$K_i$ values of 3a-3d with all three NOS isoforms[a].

| Compound | nNOS (µM) | eNOS (µM) | iNOS (µM) | selectivity[b] | |
|---|---|---|---|---|---|
| | | | | n/e | n/i |
| 3a | 0.41 | 40 | 44 | 98 | 105 |
| 3b | 0.82 | 77 | 114 | 93 | 139 |
| 3c | 0.39 | 37 | 57 | 93 | 143 |
| 3d | 0.40 | 66 | 36 | 169 | 92 |

[a]The $K_i$ values were calculated based on the directly measured $IC_{50}$ values (see examples, below), which represent at least duplicate measurements with standard deviations of ±10%.
[b]The ratio of $K_i$ (eNOS or iNOS) to $K_i$ (nNOS).

The cellular potencies of these compounds were measured from the inhibition of the production nitric oxide in HEK293t cells stably expressing nNOS (Table 2). Comparing the $IC_{50}$ values of all compounds in the purified enzyme assay versus the cellular assay clearly indicates that permeability limits the effective concentration inhibitors within cells. However, in comparison to 1 and 2, 3c and 3d are similar in permeability while 3a and 3b clearly show improved penetration. Without limitation, the difference in membrane penetration between 3a-b and 3c-d, may also be a result of the hydrophilic nature of the phenol and the furan substituents of 3c and 3d, respectively, in comparison with the more lipophilic fluorophenyl and methoxyphenyl substituents of 3a and 3b, respectively.

TABLE 2

$IC_{50}$ values of NOS inhibitors in purified enzyme assay and cell-based assay.

| Compound | In vitro $IC_{50}$ (µM) | Cell-based $IC_{50}$ (µM) | Relationship (fold higher in cells) |
|---|---|---|---|
| 1 | 0.45 | 325 | 722 x |
| 2 | 1.0 | 125 | 125 x |
| 3a | 3.6 | 120 | 33 x |
| 3b | 7.1 | 190 | 27 x |
| 3c | 3.5 | 520 | 150 x |
| 3d | 3.4 | 420 | 123 x |
| Aminopyridine[a] | 0.05 | 25 | 500x |
| L-NNA[b] | 5.0 | 5.0 | 1 |

[a]aminopyridine = 2-amino-4,6-dimethylaminopyridine hydrochloride.
[b]L-NNA = L-N-nitroarginine, a NOS inhibitor known to be cell-permeable.

Furthermore, Table 2 shows that while 2 and 3a have similar $IC_{50}$ values in the cell-based assay, when compared to their potencies in the purified enzyme assay, the cell-based $IC_{50}$ value of 3a is only 33 times higher than its in vitro $IC_{50}$, while the cell-based $IC_{50}$ value of 2 is 125 higher than its in vitro potency. Compounds 3a and 3b have slightly weaker inhibition of nNOS directly, as reported by their in vitro $IC_{50}$ values, but a cell-based $IC_{50}$ value close to that of 2. This suggests that 3a and 3b have significantly higher permeability. The aminopyridine fragment alone (2-amino-4,6-dimethylaminopyridine) was also tested to comparatively evaluate the membrane permeability of this moiety of our nNOS inhibitors. This aminopyridine has a $pK_a$ of ~7, and will therefore be partially protonated at physiological pH. It has moderate cell-based potency, and a similar low micromolar in vitro potency, suggesting that this fragment is actually quite membrane-permeable.

Figure 3A:
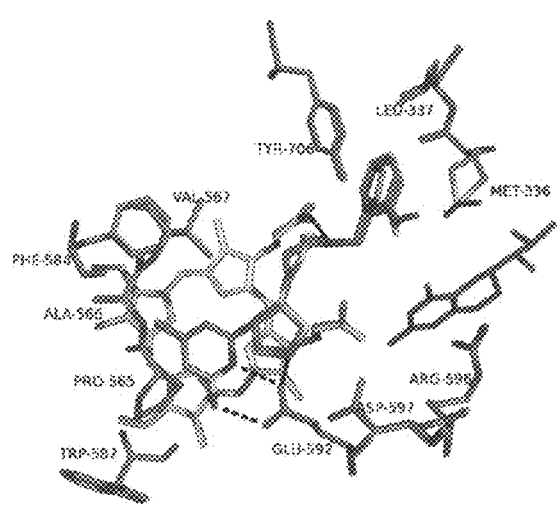
FIGS. 3A-B. A. Crystallographic binding conformations of compounds 3a-3d (overlaid). 3a (green), 3b cyan, 3c yellow, 3d magenta, heme is shown in light pink; H₄B is blue. Residues in the structures of 3a-3c overlay nearly perfectly so only 3a is shown. Residues of 3d (the furan-containing inhibitor) are also shown (magenta) because of the difference in the configuration of Met336. B. Crystallographic binding conformations of 1 (3JWS, cyan), 2 (3NLK, magenta) and 3a (green), overlaid. Residues overlay nearly perfectly, so only those corresponding to the crystal structure of 3a are shown.
Figure 3B:
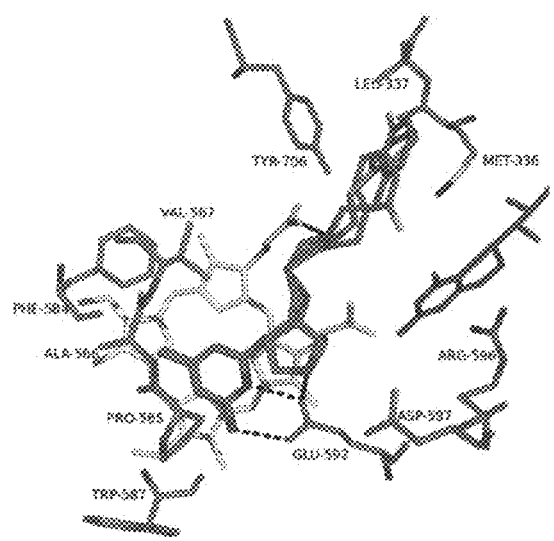

Crystal structures of all four compounds in the nNOS active site were obtained (FIG. 3). Like 1 and 2, compounds 3a-3d all bind the nNOS active site in a "normal binding mode", with the 2-amino-4-methylpyridine binding over the heme iron and interacting with Glu592. The pyrrolidine nitrogen hydrogen bonds with Glu592, and interacts near Asp597, the residue that can be exploited for selectivity between nNOS and eNOS (Asn368). The nitrogen of the substituted phenylmethyamino (or furanmethylamino) hydrogen bonds with heme propionate D in all 4 inhibitors. The substituted phenyls or the furan occupy the pocket lined with hydrophobic residues Met336, Leu337, Tyr709. There are small differences in the orientation of the carbon chain between the pyrrolidine and the amine that engages in hydrogen bonding with the heme propionate. Another difference is that in the crystal structure of 3d, which contains the furan in place of the phenyl substituents of 3a-c, Met336 is rotated in closer to the inhibitor molecule which the smaller furan is able to accommodate. FIG. 3B shows the overlay of previously designed inhibitors 1 and 2 with 3a. Inhibitor 1 contains a nitrogen in place of the oxygen atoms off of the pyrrolidine moiety in 2 and 3a-d, but the more noticeable difference is between inhibitors 1 and 2 and inhibitor 3: in the latter, one less methylene unit in the carbon chain to the phenyl substituent. The hydrophobic pocket is large enough to accommodate either chain length, and although these inhibitors adapt slightly different conformations, there are no significant changes in the residues in this pocket. The slightly higher $K_i$ of compound 3b, the methoxy-substituted inhibitor, may be due to a slight steric clash with Met336 in this pocket.

As demonstrated by the following representative examples, a new series of chiral nNOS inhibitors can be synthesized. Without limitation, through an intramolecular hydrogen bond, representative inhibitor compounds 3a-d can form a "closed" conformation, which provides enhanced lipophilicity and therefore, improved membrane and BBB permeability. When binding to a target nNOS, inhibitors 3a-d can release the secondary amino group to adopt an "open" conformation—to maintain the high potency and isozyme selectivity of corresponding parent compound.

EXAMPLES OF THE INVENTION

The following non-limiting examples and data illustrate various aspects and features relating to the compounds, compositions and/or methods of the present invention, including the use of intramolecular hydrogen bonding to improve the efficacy of such compounds, as are available through the synthetic methodologies described herein. In comparison with the prior art, the present compounds, compositions and/or methods provide results and data which are surprising, unexpected and contrary thereto. While the utility of this invention is illustrated through the use of several compounds, moieties thereof and groups thereon, it will be understood by those skilled in the art that comparable results are obtainable with various other compounds and moieties/groups, as are commensurate with the scope of this invention.

Example 1

(3S,4S)-tert-Butyl 3-(allyloxy)-4-((6-(bis(tert-butoxycarbonyl)amino)-4-methylpyridin-2-yl)methyl)pyrrolidine-1-carboxylate (5). To a solution of 4 (1.15 g, 2.0 mmol) and Pd(Ph$_3$P)$_4$ (235 mg, 0.2 mmol) in dry THF (50 mL) was added allyl methyl carbonate (700 µL, 6.0 mmol). (See, Haight, A. R.; Stoner, E. J.; Peterson, M. J.; Grover, V. K. General method for the palladium-catalyzed allylation of aliphatic alcohols. *J. Org. Chem.* 2003, 68, 8092-8096.) The reaction mixture was allowed to stir at 45° C. for 5 h, and then concentrated. The resulting material was purified by flash column chromatography (silica gel, EtOAc/hexanes, 1:2, R$_f$=0.40) to yield 5 (675 .g, 66%) as a colorless oil: $^1$H NMR (500 MHz, CDCl$_3$) δ 1.40-1.50 (m, 27H), 2.25-2.27 (m, 3H), 2.60-2.75

(m, 1H), 2.78-2.85 (dd, J=9.0, 13.5 Hz, 1H), 2.98-3.05 (dd, J=9.0, 13.5 Hz, 1H), 3.10-3.21 (m, 1H), 3.25-3.29 (dd, J=4.0, 12.5 Hz, 1H), 3.40-3.62 (m, 2H), 3.75-3.85 (m, 2H), 4.00-4.10 (td, J=5.5, 13.0 Hz, 1H), 5.15-5.17 (d, J=10.5 Hz, 1H), 5.25-5.29 (d, J=17.0 Hz, 1H), 5.84-5.91 (ddd, J=5.0, 10.5, 17.0 Hz, 1H), 6.85-6.95 (m, 2H); $^{13}$CNMR (125 MHz, CDCl$_3$) δ 20.9, 27.9, 28.4, 28.5, 34.7, 34.8, 42.7, 43.3, 48.9, 49.2, 50.4, 51.0, 70.2, 70.3, 77.8, 78.6, 79.1, 79.2, 82.8, 116.7, 116.9, 119.6, 122.9, 134.6, 134.7, 149.50, 149.52, 151.4, 151.5, 151.8, 154.5, 154.8, 159.2, 159.3; LC-TOF (M+H$^+$) calcd for C$_{29}$H$_{46}$N$_3$O$_7$ 548.3336. found 548.3339.

Example 2

(3S,4S)-tert-Butyl 3-((6-(bis(tert-butoxycarbonyl)amino)-4-methylpyridin-2-yl)methyl)-4-(2-oxoethoxy)pyrrolidine-1-carboxylate (6). A solution of 5 (100 mg, 0.19 mmol) in CH$_2$Cl$_2$ (10 mL) was cooled to −78° C., to which O$_3$ was charged until the reaction solution turned purple (~10 min). The O$_3$ flow was stopped, and the reaction was allowed to stir at the same temperature for 30 min. To the resulting solution was added Me$_2$S (150 μL). The reaction mixture was then warmed to room temperature and kept stirring at room temperature for an additional 2 h. The solvent was removed by rotary evaporation and the resulting crude product was purified by flash column chromatography (EtOAc/hexanes, 1:1, R$_f$=0.2) to yield 6 (87 mg, 87%) as a colorless oil: $^1$H NMR (500 MHz, CDCl$_3$) δ 1.45 (s, 27H), 2.22 (s, 3H), 2.70-2.85 (m, 111), 2.85-2.95 (m, 1H), 3.05-3.15 (m, 1H), 3.16-3.25 (m, 1H), 3.30-3.37 (m, 1H), 3.45-3.70 (m, 2H), 3.85-3.95 (m, 2H), 4.05-4.20 (t, J=10.0 Hz, 1H), 6.90-6.93 (m, 2H), 9.66 (s, −1H); $^{13}$C NMR (125 MHz, CDCl$_3$) δ 20.9, 24.7, 27.9, 28.5, 29.7, 34.4, 42.5, 43.2, 48.8, 49.1, 50.3, 51.0, 74.6, 74.9, 79.4, 79.5, 80.4, 83.0, 119.66, 119.73, 122.8, 149.7, 149.8, 151.57, 151.60, 151.8, 154.4, 154.8, 159.87, 158.94, 200.2, 200.6; LC-TOF (M+H$^+$) calcd for C$_{28}$H$_{44}$N$_3$O$_8$ 550.3128. found 550.3130.

Example 3

(3S,4S)-tert-Butyl 3-((6-(bis(tert-butoxycarbonyl)amino)-4-methylpyridin-2-yl)methyl)-4-(2-(2-fluorobenzylamino)ethoxy)pyrrolidine-1-carboxylate (7a). To a solution of aldehyde 6 (100 mg, 0.18 mmol) in DCM (4 mL) was added (2-fluorophenyl)methanamine (45 mg, 0.36 mmol), triethylamine (11 μL, 0.36 mmol), followed by NaHB(OAc)$_3$ (100 mg, 0.45 mmol). The reaction mixture was stirred for an additional 3 h and then concentrated. The crude product was purified by flash column chromatography (EtOAc/hexanes, 1:1, R$_f$=0.15) to yield 7a (115 mg, 91%) as a colorless oil: $^1$H NMR (500 MHz, CDCl$_3$) δ 1.43-1.44 (s, 27H), 2.29-2.30 (m, 3H), 2.60-2.75 (m, 1H), 2.76-2.85 (m, 2H), 2.92-3.00 (m, 1H), 3.05-3.14 (m, 1H), 3.20-3.50 (m, 5H), 3.52-3.70 (m, 2H), 3.72-3.80 (m, 1H), 3.91 (s, 2H), 6.84-6.85 (d, J=8.0 Hz, 1H), 6.89-6.91 (d, J=10.0 Hz, 1H), 7.02-7.06 (dd, J=9.0, 9.5 Hz, 1H), 7.10-7.13 (dd, J=7.0, 7.5 Hz, 1H), 7.20-7.30 (m, 1H), 7.35-7.40 (m, 1H); $^{13}$C NMR (125 MHz, CDCl$_3$) δ 20.9, 24.7, 27.9, 28.47, 28.50, 29.7, 34.6, 34.7, 36.6, 42.6, 43.3, 46.8, 48.2, 48.8, 49.1, 50.3, 50.8, 68.0, 68.2, 78.7, 79.2, 79.3, 79.4, 82.8, 115.2, 115.3, 115.4, 115.5, 119.5, 119.6, 122.8, 124.17, 124.19, 128.89, 128.92, 128.95, 128.99, 130.46, 130.51, 130.55, 149.6, 151.4, 151.5, 151.8, 154.5, 154.8, 159.08, 159.14, 160.3, 162.2; LC-TOF (M+H$^+$) calcd for C$_{35}$H$_{52}$FN$_4$O$_7$ 659.3820. found 659.3818.

Example 4

(3S,4S)-tert-Butyl 3-((6-(bis(tert-butoxycarbonyl)amino)-4-methylpyridin-2-yl)methyl)-4-(2-(2-methoxybenzylamino)ethoxy)pyrrolidine-1-carboxylate (7b). Compound 7b was synthesized using a similar procedure to that of 7a (88%): $^1$H NMR (500 MHz, CDCl$_3$) δ 1.42-1.43 (s, 27H), 2.31-2.33 (m, 3H), 2.60-2.70 (m, 1H), 2.70-2.80 (m, 1H), 2.90-3.10 (m, 4H), 3.28-3.32 (m, 1H), 3.35-3.52 (m, 3H), 3.65-3.75 (m, 1H), 3.79-3.81 (m, 2H), 3.85-3.87 (m, 3H), 4.01-4.20 (m, 2H), 6.75-7.00 (m, 4H), 7.26-7.30 (m, 1H), 7.35-7.40 (m, 1H); $^{13}$C NMR (125 MHz, CDCl$_3$) δ 20.9, 21.9, 27.9, 28.3, 28.4, 28.5, 29.7, 34.4, 34.5, 42.5, 43.2, 46.1, 47.5, 47.7, 48.7, 48.9, 50.3, 50.8, 55.4, 55.5, 60.4, 65.2, 65.3, 79.3, 79.4, 79.8, 82.92, 82.94, 110.5, 110.6, 119.7, 119.8, 121.0, 121.2, 121.3, 122.7, 122.8, 130.50, 130.52, 131.4, 149.9, 151.47, 151.51, 151.77, 151.79, 154.5, 154.7, 157.7, 158.89, 158.91, 176.2; LC-TOF (M+H$^+$) calcd for C$_{36}$H$_{55}$N$_4$O$_8$ 671.4020. found 671.4016.

Example 5

(3S,4S)-tert-Butyl 3-((6-(bis(tert-butoxycarbonyl)amino)-4-methylpyridin-2-yl)methyl)-4-(2-(2-hydroxybenzylamino)ethoxy)pyrrolidine-1-carboxylate (7c). Compound 7c was synthesized using a similar procedure to that of 7a (55%): $^1$H NMR (500 MHz, CDCl$_3$) δ 1.45-1.46 (s, 27H), 2.34 (s, 3H), 2.60-2.75 (m, 2H), 2.75-2.85 (m, 1H), 2.85-3.00 (m, 2H), 3.00-3.07 (m, 1H), 3.07-3.20 (m, 1H), 3.20-3.33 (m, 1H), 3.33-3.51 (m, 3H), 3.51-3.65 (m, 1H), 3.65-3.74 (m, 2H), 3.74-3.90 (m, 1H), 4.00-4.18 (m, 2H), 6.75-6.85 (m, 2H), 6.93 (s, 1H), 7.02-7.10 (m, 1H), 7.15-7.20 (m, 1H); $^{13}$C NMR (125 MHz, CDCl$_3$) δ 20.9, 21.1, 27.9, 28.5, 29.7, 34.1, 42.4, 43.1, 46.8, 47.0, 48.4, 48.9, 50.1, 50.3, 50.7, 50.8, 53.4, 60.3, 66.3, 66.4, 78.6, 79.3, 79.5, 79.6, 82.9, 83.2, 833, 116.1, 116.3, 118.9, 119.4, 119.7, 120.3, 120.5, 120.9, 122.9, 123.0, 123.2, 128.8, 128.9, 129.4, 129.6, 129.7, 150.3, 150.6, 151.4, 151.6, 151.7, 154.7, 154.9, 157.2, 157.3, 159.1, 159.2; LC-TOF (M+H$^+$) calcd for C$_{35}$H$_{53}$N$_4$O$_8$ 657.3863. found 657.3874.

Example 6

(3S,4S)-tert-Butyl 3-((6-(bis(tert-butoxycarbonyl)amino)-4-methylpyridin-2-yl)methyl)-4-(2-(furan-2-ylmethylamino)ethoxy)pyrrolidine-1-carboxylate (7d). Compound 7b was synthesized using a similar procedure to that of 7a (90%): $^1$H NMR (500 MHz, CDCl$_3$) δ 1.43-1.44 (s, 27H), 2.30-2.32 (m, 3H), 2.50-2.60 (m, 1H), 2.75-2.83 (m, 2H), 2.92-3.17 (m, 3H), 3.20-3.50 (m, 5H), 3.52-3.70 (m, 2H), 3.77-3.80 (m, 1H), 3.81 (s, 2H), 6.20-6.21 (d, J=3.0 Hz, 1H), 6.32 (s, 1H), 6.86-6.92 (m, 2H), 7.37 (s, 1H); $^{13}$C NMR (125 MHz, CDCl$_3$) δ 19.1, 20.9, 21.0, 23.4, 24.7, 27.9, 28.39, 28.48, 28.51, 29.7, 30.6, 34.6, 34.7, 36.6, 42.6, 43.2, 45.8, 45.9, 48.2, 48.3, 48.8, 49.1, 50.3, 50.8, 64.4, 68.2, 68.4, 78.7, 79.2, 79.3, 79.4, 82.85, 82.86, 107.0, 107.2, 110.16, 110.24, 119.57, 119.61, 122.8, 141.90, 141.94, 141.97, 149.6, 151.45, 151.50, 151.8, 153.4, 154.5, 154.7, 159.1, 159.2, 171.3; LC-TOF (M+H$^+$) calcd for C$_{33}$H$_{51}$N$_4$O$_8$ 631.3703. found 631.3703.

Example 7

6-(((3S,4S)-4-(2-(2-Fluorobenzylamino)ethoxy)pyrrolidin-3-yl)methyl)-4-methylpyridin-2-amine (3a). To a solution of 7a (70 mg, 0.10 mmol) in MeOH (2 mL) was added 6 N HCl (4 mL) at room temperature. The mixture was stirred for 12 h and then concentrated. The crude product was purified by recrystallization (EtOH/H$_2$O) to give inhibitor 3a (38 mg, 97%): $^1$H NMR (500 MHz, D$_2$O) δ 2.18 (s, 3H), 2.68-2.73 (m, 1H), 2.76-2.82 (dd, J=7.0, 15.5 Hz, 1H), 2.85-2.90

(dd, J=8.0, 15.0 Hz, 1H), 3.04-3.09 (t, J=11.5 Hz, 1H), 3.15-3.25 (m, 2H), 3.39-3.43 (dd, J=8.5, 11.5 Hz, 1H), 3.50-3.53 (d, J=13.5 Hz, 1H), 3.53-3.60 (m, 1H), 3.73-3.80 (m, 1H), 4.05-4.10 (m, 1H), 4.22 (s, 2H), 6.47 (s, 1H), 6.53 (s, 1H), 7.12-7.14 (dd, J=1.0, 8.5 Hz, 1H), 7.16-7.18 (dd, J=1.0, 8.0 Hz, 1H), 7.35-7.40 (m, 1H); $^{13}$C NMR (125 MHz, D$_2$O) δ 21.0, 28.8, 41.3, 44.67, 44.70, 46.4, 47.1, 49.3, 63.9, 78.0, 110.3, 114.0, 115.8, 115.9, 117.4, 117.5, 125.0, 125.1, 132.1, 132.2, 132.3, 132.4, 145.7, 153.8, 158.1, 160.1, 162.0; LC-TOF (M+H) calcd for C$_{20}$H$_{28}$FN$_4$O 359.2247. found 359.2253.

Example 8

6-(((3S,4S)-4-(2-(2-Methoxybenzylamino)ethoxy)pyrrolidin-3-yl)methyl)-4-methylpyridin-2-amine (3b). Compound 3b was synthesized using a similar procedure to that of 3a (96%): $^1$H NMR (500 MHz, CDCl$_3$) δ 2.18 (s, 3H), 2.65-2.85 (m, 3H), 3.03-3.10 (t, J=11.5 Hz, 1H), 3.17-3.32 (m, 3H), 3.40-3.47 (dd, J=8.5, 12.0 Hz, 1H), 3.50-3.57 (m, 2H), 3.72-3.80 (m, 4H), 4.05-4.17 (m, 3H), 6.43 (s, 1H), 6.49 (s, 1H), 6.91-6.94 (dd, J=7.0, 7.5 Hz, 1H), 6.97-6.99 (d, J=8.5 Hz, 1H), 7.23-7.25 (dd, J=1.0, 7.5 Hz, 1H), 7.34-7.38 (ddd, J=1.5, 8.5, 9.0 Hz, 1H); $^{13}$C NMR (125 MHz, CDCl$_3$) δ 21.0, 38.7, 41.0, 46.2, 46.9, 47.1, 49.1, 55.4, 64.0, 77.8, 110.3, 111.2, 113.8, 118.2, 121.0, 131.6, 131.8, 145.6, 153.8, 157.6, 158.0; LC-TOF (M+H$^+$) calcd for C$_{21}$H$_{31}$N$_4$O$_2$ 371.2447. found 371.2450.

Example 9

2-((2-((3S,4S)-4-((6-Amino-4-methylpyridin-2-yl)methyl)pyrrolidin-3-yloxy)ethylamino)methyl)phenol (3c). Compound 3c was synthesized using a similar procedure to that of 3a (92%): $^1$H NMR (500 MHz, CDCl$_3$) δ 2.15 (s, 3H), 2.60 2.70 (m, 1H), 2.77-2.82 (m, 2H), 3.00-3.10 (t, J=11.5 Hz, 1H), 3.18-3.22 (m, 3H), 3.42-3.51 (dd, J=8.5, 11.5 Hz, 1H), 3.51-3.56 (m, 2H), 3.73-3.80 (m, 1H), 4.00-4.25 (m, 3H), 6.38 (s, 1H), 6.50 (s, 1H), 6.83-6.88 (m, 2H), 7.21-7.25 (m, 2H); $^{13}$C NMR (125 MHz, CDCl$_3$) δ 21.0, 28.8, 41.2, 46.0, 47.0, 47.1, 49.2, 63.7, 77.8, 110.3, 114.0, 115.4, 117.0, 120.6, 131.6, 131.7, 145.6, 153.8, 155.0, 158.0; LC-TOF (M+H$^+$) calcd for C$_{20}$H$_{29}$N$_4$O$_2$ 357.2291. found 357.2277.

Example 10

6-(((3S,4S)-4-(2-(Furan-2-ylmethylamino)ethoxy)pyrrolidin-3-yl)methyl)-4-methylpyridin-2-amine (3d). Compound 3b was synthesized using a similar procedure to that of 3a (96%): $^1$H NMR (500 MHz, CDCl$_3$) δ 2.32 (s, 3H), 2.65-2.73 (m, 1H), 2.76-2.83 (dd, J=7.5, 15.0 Hz, 1H), 2.88-2.93 (dd, J=7.5, 14.5 Hz, 1H), 3.04-3.09 (t, J=11.5 Hz, 1H), 3.17-3.24 (m, 3H), 3.39-3.43 (dd, J=9.0, 11.5 Hz, 1H), 3.48-3.51 (d, J=13.5 Hz, 2H), 3.51-3.56 (m, 1H), 3.70-3.75 (m, 1H), 4.05-4.10 (m, 1H), 4.22 (s, 2H), 6.38-6.40 (dd, J=2.0, 5.0 Hz, 1H), 5.48 (s, 1H), 6.52-6.53 (d, J=3.5 Hz, 1H), 6.55 (s, 1H), $^{13}$C NMR (125 MHz, CDCl$_3$) δ 21.0, 28.8, 41.4, 43.1, 46.0, 47.0, 49.4, 64.0, 78.1, 110.3, 110.8, 111.0, 113.0, 114.0, 144.1, 144.3, 144.9, 145.8, 153.9, 158.1; LC-TOF (M+H$^+$) calcd for C$_{18}$H$_{27}$N$_4$O$_2$ 331.2134. found 331.2136.

Example 11

In Vitro Enzyme Assays

The three NOS isoforms, rat nNOS, murine iNOS and bovine eNOS were recombinant enzymes overexpressed in E. coli and purified as reported in the literature. (See, e.g., example 51 of the aforementioned incorporated '790 patent and the references cited therein.) The hemoglobin capture was used to measure nitric oxide production. (See, Hevel, J. M. and Marietta, M. A. Nitric Oxide Synthase Assays. Methods Enzymol. 1994, 133, 250-258.) Briefly, the assay was run at 37° C. in 100 mM HEPES buffer (10% glycerol; pH 7.4) in the presence of 10 μM L-arginine. The following NOS cofactors were also included in the assay: 100 μM NADPH, 10 μM tetrahydrobiopterin, 1 mM CaCl$_2$, 11.6 μg/mL calmodulin and 3.0 μM oxyhemoglobin. For iNOS, calmodulin and CaCl$_2$ were omitted. The assay was run in a high throughput manner, using the Synergry 4 by BioTek, at the Northwestern University HighThroughput Analysis Facility. The assay was run in triplicate; 48 100 uL reactions were ran at once in a 96 well plate. The addition of hemoglobin and NOS were automated with a maximum of a 30 second delay before the reactions could be recorded at 401 nm. The absorbance increase at 401 nm is due to the formation of NO via the conversion of oxyhemoglobin to methemoglobin.

The IC$_{50}$ values were obtained using non-linear regression in GraphPad Prism5 software. Subsequent K$_i$ values were determined using the well-known Cheng-Prusoff relationship: $K_i = IC_{50}/(1+[S]/K_m)$ The following known K$_m$ values were used: rat nNOS 1.3 μM; murine iNOS 8.3 μM; bovine eNOS 1.7 μM.

Example 12 nNOSCell Based Assay

HEK293t cells stably transfected with rat nNOS were cultured as previously described, and the nNOS inhibition assay was performed as previously reported (Fang, J.; Silverman, R. B. A cellular model for screening neuronal nitric oxide synthase inhibitors. Analytical Biochemistry 2009, 390, 74-78), with the following modifications: assays were performed in 96-well plates with a total volume of 100 μL, and 10 μM A23187 (Sigma Aldrich, St Louis, Mo., USA) in 50% DMSO was used in place of 5 μM. Nine concentrations of each inhibitor were tested, in at least triplicate wells. All inhibitors were assayed within the same experiment to assure consistencies in cell concentration and passage number. The entire assay was repeated at least twice for each inhibitor, and the IC$_{50}$ values averaged. After 6 hours of activation (in the presence or absence of inhibitor, which was added 30 minutes before activation) 50 μL aliquots of the media were removed and nitrite production was quantified using Griess reagent. (See, Hevel, J. M.; White, K. A.; Marietta, M. Purification of the inducible murine macrophage nitric oxide synthase. Identification as a flavoprotein. J. Biol. Chem. 1991, 266, 22789-22791.)

We claim:
1. A compound selected from compounds of a formula

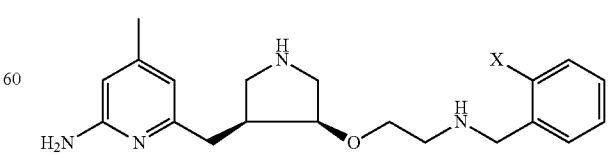

wherein X is selected from fluoro, hydroxy and methoxy groups, said compound in a conformation for intramolecular hydrogen-bonding; and salts thereof.

2. The compound of claim 1 wherein X is selected from fluoro and methoxy groups.

3. The compound of claim 1 wherein said compound is an ammonium salt, and said salt has a counter ion that is a conjugate base of a protic acid.

4. A compound selected from compounds of a formula

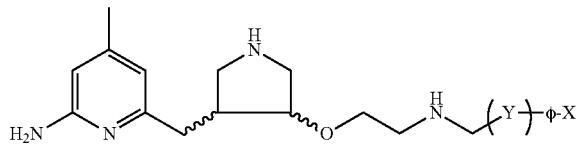

wherein X is selected from hydroxy and methoxy groups; and salts thereof.

5. The compound of claim 4 wherein X is a methoxy group.

6. The compound of claim 4 wherein said compound is an ammonium salt, and said salt has a counter ion that is a conjugate base of a protic acid.

7. A compound selected from compounds of a formula

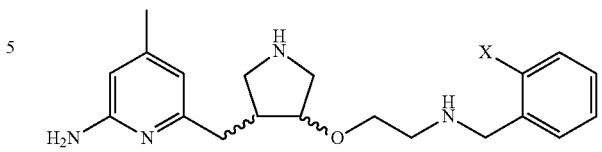

wherein X is selected from fluoro, hydroxyl and methoxy groups; and salts thereof.

8. The compound of claim 7 wherein X is selected from fluoro and methoxy groups.

9. The compound of claim 7 wherein said compound is an ammonium salt, and said salt has a counter ion that is a conjugate base of a protic acid.

10. The compound of claim 7 comprising a cis diastereomeric configuration.

* * * * *